United States Patent
Widmer et al.

(10) Patent No.: US 10,219,795 B2
(45) Date of Patent: Mar. 5, 2019

(54) OCCLUDER

(71) Applicant: CARAG AG, Baar (CH)

(72) Inventors: Beat Widmer, Lucerne (CH); Andreas Mellmann, Baar (CH)

(73) Assignee: CARAG AG, Baar (CH)

( * ) Notice: Subject to any disclaimer, the term of this patent is extended or adjusted under 35 U.S.C. 154(b) by 7 days.

(21) Appl. No.: 15/028,023

(22) PCT Filed: Oct. 6, 2014

(86) PCT No.: PCT/EP2014/071327
§ 371 (c)(1),
(2) Date: Apr. 7, 2016

(87) PCT Pub. No.: WO2015/052125
PCT Pub. Date: Apr. 16, 2015

(65) Prior Publication Data
US 2016/0249898 A1 Sep. 1, 2016

(30) Foreign Application Priority Data

Oct. 10, 2013 (EP) ..................................... 13188121

(51) Int. Cl.
*A61B 17/00* (2006.01)
*A61B 90/00* (2016.01)
*A61B 17/12* (2006.01)

(52) U.S. Cl.
CPC .... *A61B 17/0057* (2013.01); *A61B 17/12031* (2013.01); *A61B 17/12122* (2013.01);
(Continued)

(58) Field of Classification Search
CPC .......... A61B 17/0057; A61B 17/12031; A61B 17/12122; A61B 17/12145;
(Continued)

(56) References Cited

U.S. PATENT DOCUMENTS

| 6,488,706 B1 | 12/2002 | Solymar |
| 2002/0068950 A1* | 6/2002 | Corcoran ........... A61B 17/0057 606/153 |

(Continued)

FOREIGN PATENT DOCUMENTS

| EP | 2524653 | 11/2012 |
| EP | 2524653 A1 * | 11/2012 ......... A61B 17/0057 |

(Continued)

OTHER PUBLICATIONS

International Search Report and Written Opinion for Int. App. No. PCT/EP2014/071327, completed Jan. 15, 2015.

*Primary Examiner* — Todd J Scherbel
*Assistant Examiner* — Brooke Labranche
(74) *Attorney, Agent, or Firm* — McDonnell Boehnen Hulbert & Berghoff LLP (57) ABSTRACT

An occluder including at least one occluding body, a multiple of elongate members forming an expanding unit capable of expanding into at least one fixation structure for fixing the occluding body within the passage thereby expanding the occluding body), the elongate members penetrating the occluding body, a locking unit for locking the expanding unit in its expanded state, fixation bushes for restricting relative movement between the elongate members and the occluding body, each fixation bush surrounding one single elongate member and abutting the occluding body, at least one thread and wherein at least one of these fixation bushes is fastened to the at least one occluding body with this at least one thread, the thread penetrating the at least one bush and the occluding body.

16 Claims, 9 Drawing Sheets

(52) U.S. Cl.
CPC ........ *A61B 17/12145* (2013.01); *A61B 90/39* (2016.02); *A61B 2017/00004* (2013.01); *A61B 2017/00477* (2013.01); *A61B 2017/00575* (2013.01); *A61B 2017/00592* (2013.01); *A61B 2017/00597* (2013.01); *A61B 2017/00606* (2013.01); *A61B 2017/00619* (2013.01); *A61B 2090/3966* (2016.02)

(58) Field of Classification Search
CPC ........... A61B 2017/00575; A61B 2017/00606; A61B 2017/00619; A61B 2090/3966; A61B 2017/00004; A61B 2017/00477; A61B 2017/00592; A61B 2017/00597; A61B 90/39

See application file for complete search history.

(56) References Cited

U.S. PATENT DOCUMENTS

| | | | |
|---|---|---|---|
| 2003/0149463 | A1 | 8/2003 | Solymar et al. |
| 2004/0143294 | A1* | 7/2004 | Corcoran ........... A61B 17/0057 606/213 |
| 2005/0034723 | A1 | 2/2005 | Bennett et al. |
| 2012/0179190 | A1* | 7/2012 | Stoop ................. A61B 17/0057 606/191 |

FOREIGN PATENT DOCUMENTS

| | | | |
|---|---|---|---|
| WO | 03/061481 | 7/2003 | |
| WO | WO 03061481 A1 * | 7/2003 | ......... A61B 17/0057 |
| WO | 2004/067538 | 8/2004 | |
| WO | 2005/074813 | 8/2005 | |
| WO | 2006/062711 | 6/2006 | |
| WO | 2010/129511 | 11/2010 | |
| WO | 2012/156415 | 11/2012 | |

* cited by examiner

OCCLUDER

CROSS REFERENCE TO RELATED APPLICATIONS

The present application is a U.S. National Phase Application pursuant to 35 U.S.C. § 371 of International Application No. PCT/EP2014/071327 filed Oct. 6, 2014, which claims priority to European Patent Application No. 13188121.1 filed Oct. 10, 2013. The entire disclosure contents of these applications are herewith incorporated by reference into the present application.

TECHNICAL FIELD

The present invention relates to an occluder for occluding a passage in a circulatory system and more particularly for closing a body passage of a human body, for example an aperture through the atrial septum or the ventricle septum of a heart or in a body channel.

BACKGROUND

U.S. Pat. No. 6,488,706 discloses a well-working implant for occluding a passage in a circulatory. This implant has its particular application as a cardiological implant by means of which it is possible, for example to close an aperture through the atrial septum or the ventricle septum of a heart. It is arranged to be deployed or built up at a desired location in the body. This occluder comprises a plurality of thin wire-like elongate members which form a fixation structure and a single occluding body, namely a disk-like flexible membrane, which is expanded by the fixation structure in the body passage. The fixation structure is locked in its expanded state by a locking unit. This locking unit comprises two locking elements which are brought together when the occluding body is expanded.

WO 2005/074813 discloses an occluder working with the same principle but comprising two occluding bodies which are expanded by the fixation structure. This occluder securely closes both sides of the passage.

These two occluders have the advantage that the occluders can be opened and closed and therefore its location within the body passage can be changed until the fixation structure is locked in its expanded form by the locking unit. However, care has to be taken that the thin elongate members, especially when bent into the fixation structure, do not break. When biodegradable material is used as suggested in U.S. 2003/0149463, care has to be taken that the implant is overgrown with the body tissue, before the material is dissolved. Small parts which would otherwise break from the occluder and be transported in other parts of the human body may cause some severe damage. Furthermore it was noticed that the overgrowth of the occluding body, especially the disk-like membranes, happens faster than the overgrowth of the elongate members.

WO 2012/156415 attends to this problem by suggesting a protecting jacket or shell being arranged around the fixation structure. This shell is made of a soft and flexible material so that it can also be compressed or folded when the occluder is introduced in an introduction sheath into an animal or human body. When parts of the fixation structure break away, they are hold back by the jacket and can not wander through the body. However, there are still parts of the occluder which can wander through the body.

Other types or occluders are known in the state of the art as well. However the prior art occluders described in the following do not have the advantages mentioned above:

WO 03/061481 discloses a sail-like occluder comprising two sheets forming the occluding bodies and wire arms. The wire arms end in tips which are sewed on the sheets.

WO 2006/062711 shows two sheet-like occluding bodies and elongate members forming an expanding structure, wherein the elongate members are sewed on the sheets.

In WO 2010/129511 the sheets are sewed to elongate members which also comprise terminating ends.

Attachments of arms to the sheets by sutures are also disclosed in WO 2004/067538 and U.S. 2005/034723.

SUMMARY

It is therefore an object of the invention to provide an improved occluder.

The inventive occluder for occluding a passage in a circulatory system comprises
- at least one occluding body for occluding the passage,
- a multiple of elongate members forming an expanding unit capable of expanding into at least one fixation structure for fixing the occluding body within the passage thereby expanding the occluding body, the elongate members penetrating the at least one occluding body,
- a locking unit for locking the expanding unit in its expanded state and
- fixation bushes for restricting relative movement between the elongate members and the at least one occluding body, each fixation bush surrounding one single elongate member and abutting one of the at least one occluding body,
- wherein the occluder further comprises at least one thread and wherein at least one of these fixation bushes is fastened to the at least one occluding body with this at least one thread, the thread penetrating the bush and the occluding body. Preferably, each of these bushes is fastened to one of the at least one occluding body.

The elongate members are preferably filaments, threads or wires. The elongate members penetrating the at least one occluding body enables an easy handling of the occluder. Fixation structures can be formed as known from WO 2012/156415, WO 2005/074813 and U.S. Pat. No. 6,488,706. In a preferred embodiment, the inventive occluder is of the same type, i.e. having one or two occluding bodies, the same locking unit and the same elongate members bending and twisting into a rosette-shaped fixation structure when the opposite ends of the elongate members are brought together.

Since the bushes which connect the at least one occluding body to the elongate members are sewed to the occluding body, these bushes remain fixed to the occluding body, even when the elongate member should break. The bushes can not wander through the animal or human body. This improves the safeness of the occluder, since especially such small and tiny parts could wander to any places of the animal or human body. Since of their tininess they can not easily be found and they can cause severe harm.

In a preferred embodiment of the invention, the at least one occluding body comprises a multiple of openings, each opening being penetrated by one single of the elongate members, wherein the at least one thread penetrates the occluding body through these openings. This simplifies production. For example, occluding bodies as known in WO 2012/156415, WO 2005/074813 and U.S. Pat. No. 6,488, 706 can be used for the inventive occluder as well.

In a preferred embodiment of the invention, the at least one thread forms a loop around each bush.

The thread can be closed by making a knot, for example with its two ends. The two ends of the thread or the two strands can also be glued or welded together.

A multiple of bushes can be attached with the same thread to the occluding body. However, in a preferred embodiment, each bush is fastened to the occluding body with a separate thread.

In a preferred embodiment of the invention, the loop is closed and each thread is forming a closed loop.

In another preferred embodiment of the invention, each thread comprises a strand with a first free end and a second free end, the first free end being located on one side of the bush and the second free end being located on a second, opposite side of the bush, and wherein the first and second free end are thicker than the strand in between. Preferably, the first free end and the second free end are bulges. For example, these bulges can be obtained by knotting the ends of the strand or by heating the ends until they shrink into bulges.

Preferred material for the bushes are preferably made of metal, such as platinum-iridium or of a degradable but X-ray-visible material such as a blend of a polymer with BaS (barium sulfate). The sewing threads are preferably made of non-degradable polymer (such as polypropylene, polyamide, polyester).

The secureness of the occluder can even be improved when the occluder comprises a shell, sheath or jacket enclosing at least some parts of the occluder. In the following, the expression jacket will be used, also meaning shell, sheath or similar items. The outer jacket is preferably enveloping a multiple or all of the elongate members, i.e. a bunch of them.

Preferably, the jacket envelops the elongate members at least partially and more preferably, the jacket envelops at least one of the fixation units. Preferably, it is always arranged around this part of the expanding unit, even before the fixation structure is formed; i.e. before the occluder is expanded. As already mentioned in the introductory part of this text, this kind of occluder prevents the enveloped broken parts from wandering through the human or animal body. In case the cavity with the jacket gets filled with coagulated blood or organized tissue, the fixation structure is embedded and broken parts do not wander either.

In a preferred embodiment, the jacket is attached to the at least one occluding body, so that they both together form a generally or almost closed chamber. Preferably, the at least one bush is arranged in this space or chamber defined by the jacket and the at least one occluding body. Preferably, all bushes are arranged within this space or chamber.

There can be only one single occluding body and exactly two fixation structures. In a preferred embodiment, the occluder comprises exactly two fixation structures and exactly two occluding bodies. Preferably there are exactly two outer jackets, each jacket enveloping one of the fixation structures.

In a preferred embodiment the occluder comprises exactly a first and a second occluding body, wherein in a non-expanded state the first and second occluding bodies are arranged at a distance from each other, wherein a first of said fixation structures is arranged between the first occluding body and the first element of the locking unit and a second of said fixation structures is arranged between the second occluding body and the second element of the locking unit.

Preferably the at least one occluding body is a flexible sheet, wherein each of the occluding bodies is preferably a separate sheet.

In a preferred embodiment, the jacket surrounds the fixation structure in its circumference around the longitudinal axis of the occluder. The jacket can be made of a tight material or it can also have openings. For example it can be a net, knitted fabric, woven fabric, a casted membrane or artificial or biological tissue. The structure of the surface of the jacket, the sheath or the envelope enhances the endotheliasation or overgrowth of occluder and tissue since tissue cells prefer the material of the jacket more than the material of the fixation structure. This enhances the overgrowth of the occluder especially in embodiments where the fixation structure adapts its shape to the tissue surrounding of the passage in the human or animal body.

Preferred material for the jacket is Polyester or a degradable polymer like PLA, PLLA, PGA, PLGA or P4HB or a blend of those polymer materials. Preferred material for the fixation structure is metal or a degradable polymer like PLA, PLLA, PGA, PLGA or P4HB or a blend of those polymer materials. The occluding body is preferably made of the same material as the jacket. However it can be made of a different material as well. Preferred materials for the occluding body are Polyester or a degradable polymer like PLA, PLLA, PGA, PLGA or P4HB or a blend of those polymer materials. The occluding body is preferably made of a flexible sheet. Preferably it has a circular disk-like shape when expanded.

When an occluder is used which has two jackets, the jackets can be made of different materials. For example one of them can be biodegradable and the other one is not. The same applies for the fixation structures and for the occluding bodies.

When the jacket is made of a biodegradable material, the fixation structure is preferably made of a biodegradable material as well. In a preferred embodiment, the rate of degradation of the jacket is smaller than the one of the fixation structure so that the fixation structure is protected by the jacket until it is well dissolved or the occluder is overgrown.

Preferably, the expanding unit is movable relative to the enveloping jacket. Like this the fixation structure can be built up within its shell without being disturbed while expanding Preferably, the jacket is attached to at least some of the elongate members, wherein the elongate members comprise a longitudinal axis each and wherein the elongate members can move relative to the jacket in direction of their corresponding longitudinal axis. Like this the fixation structure is not disturbed while expanding but it is ensured that the jacket will safely surround the fixation structure when built up. Sewing the jacket on at least some of the longitudinal members is one simple way to obtain a secure but still loose connection between fixation structure and jacket.

In a preferred embodiment, the fixation structure is expanded within the jacket, but does not penetrate the material of the jacket.

Preferably the jacket is attached to the occluding body. The occluding body can form one side of the jacket. In a preferred embodiment, the occluding body has a circumferential rim and the jacket is fixed to this rim. This attachment does not have to be leak-proof but can have holes or openings. For example, the jacket can be sewed onto the occluding body, it can be welded onto it, and it can be glued to it or otherwise connected. It is also possible that occluding body and jacket are made of one single unitary part. However in all embodiments it is preferred that the occluding body has a round and approximately flat disk-like shape when the occluder, respectively the fixation structure, is expanded. Jacket and occluding body are preferably made of a flexible material, wherein the occluding body and the jacket are compressible into a folded state.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

The occluder according to the preferred embodiments is based on the implants disclosed in WO 2012/156415. However, it can also be based on an occluder as described in WO 2005/074813; i.e. an occluder without a surrounding jacket. It can also be based on an occluder as described in U.S. Pat. No. 6,488,706 and U.S. 2003/0149463, i.e. an occluder with a single occluding body. The occluder according to the invention could also have another shape and can function in another way as described below.

The occluder is preferably used as an implant for closing an internal passage, for example an aperture in the atrial septum or the ventricle septum of a heart, a left atrial appendage or in another human or animal body channel which one wishes to close. The implant is compressible for insertion into the body. For this insertion, a delivery mechanism is used. For example, the delivery mechanism comprises an introduction sheath, two delivery catheters and a guide wire. The occluder is introduced in a body vein or artery or body vessel, and it is deployable or expansible for occluding the passage in the circulatory system when arrived at the position of the intended closing spot.

Figure 1:
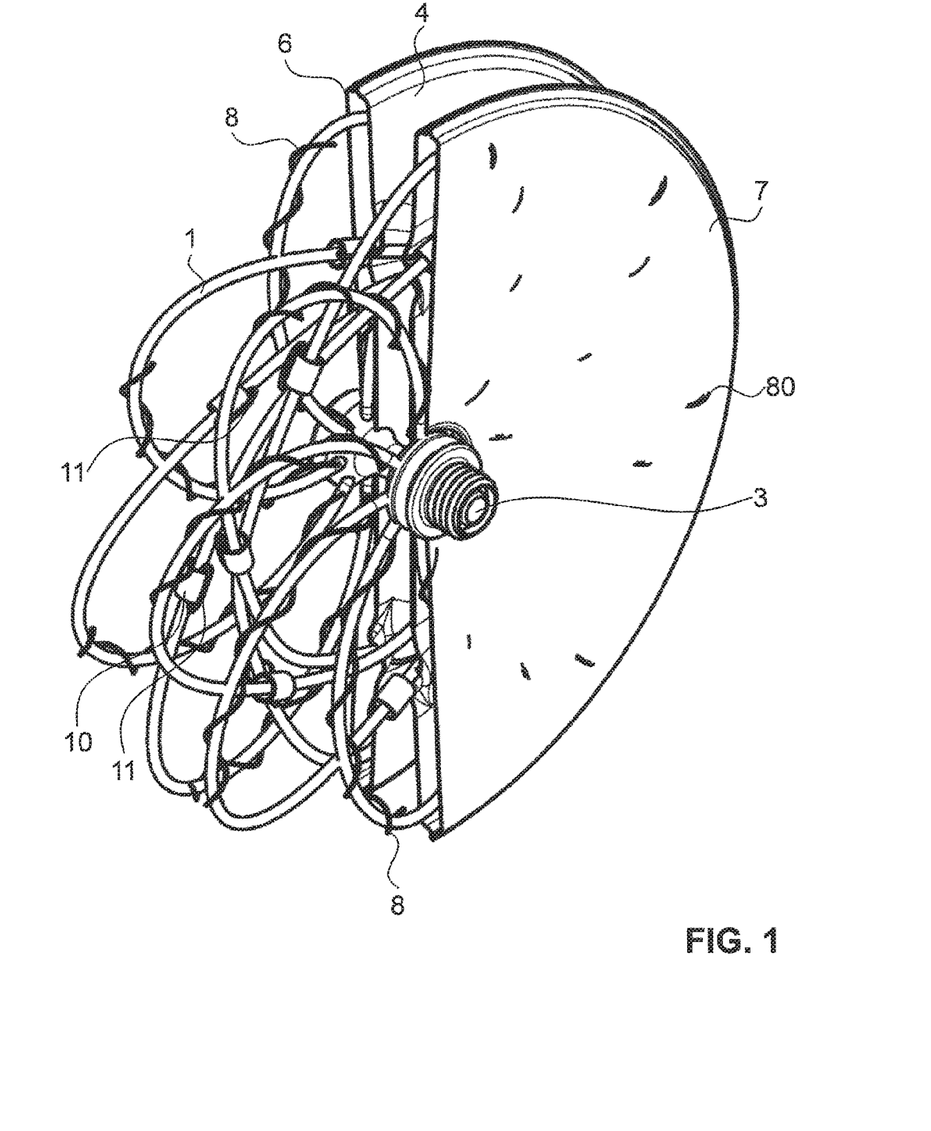
FIG. 1 shows a partial sectional view of an occluder according to the invention in an expanded state in a first embodiment.
Figure 2:
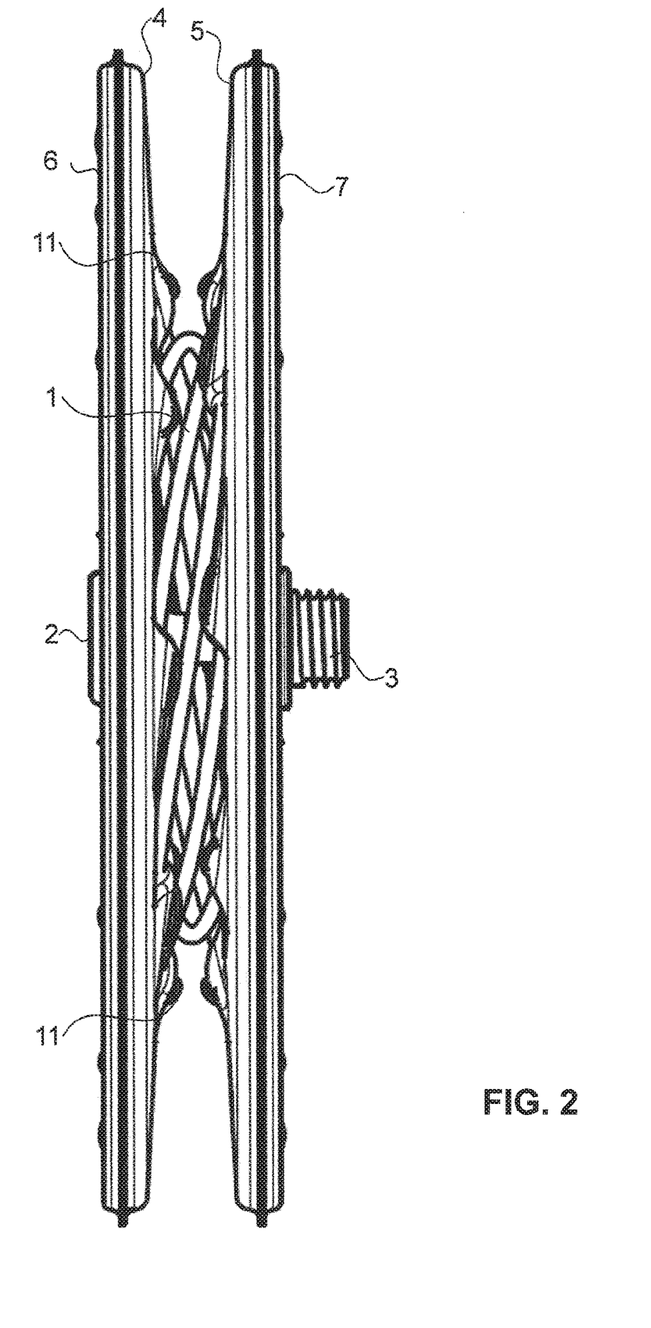
FIG. 2 shows a side view of the occluder according to FIG. 1.
Figure 3:
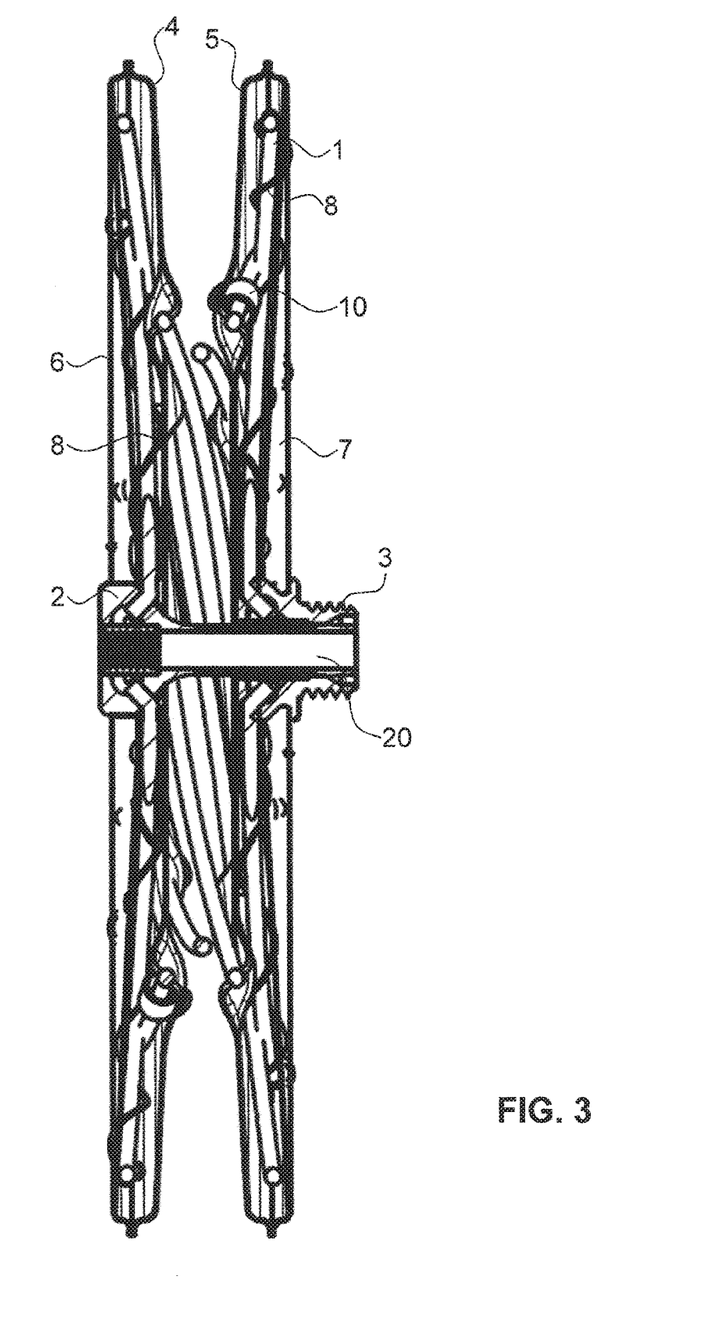
FIG. 3 shows a longitudinal section of the occluder according to FIG. 1.
Figure 4:
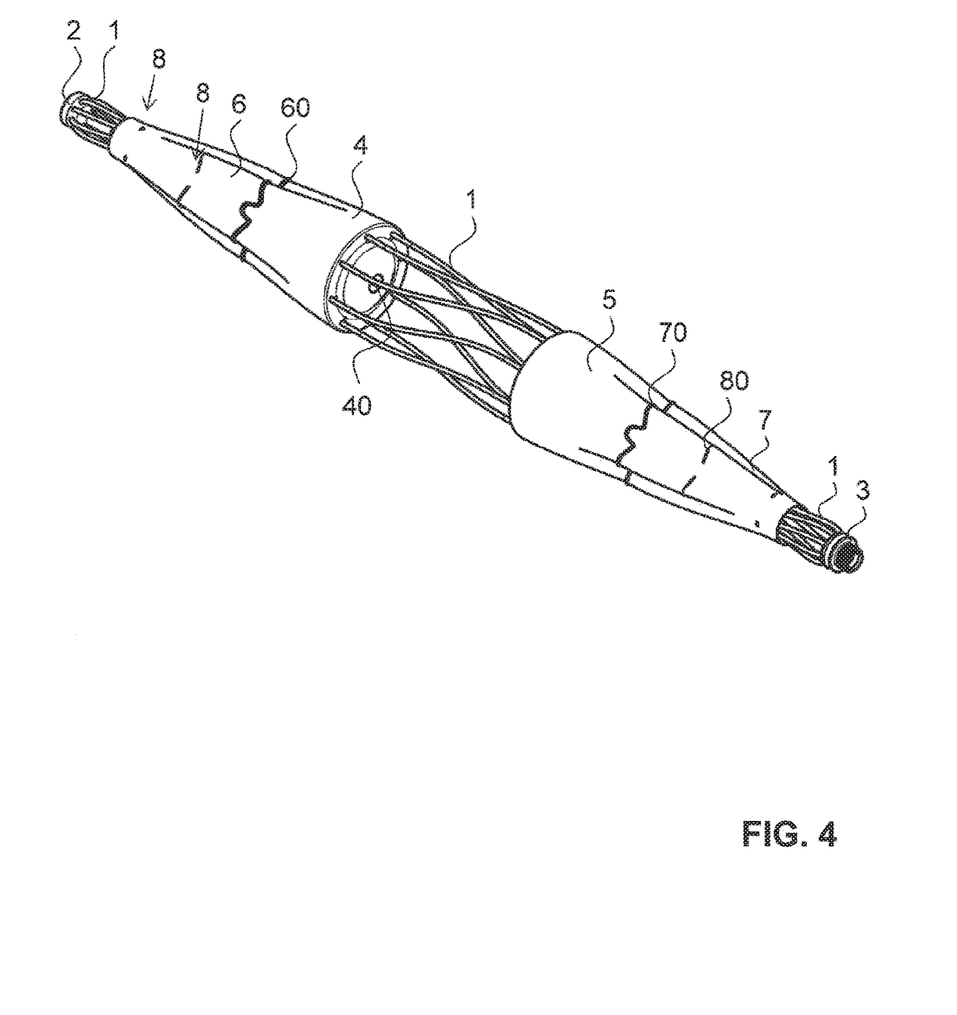
FIG. 4 shows the occluder according to a second embodiment in an almost completely compressed state.
Figure 5:
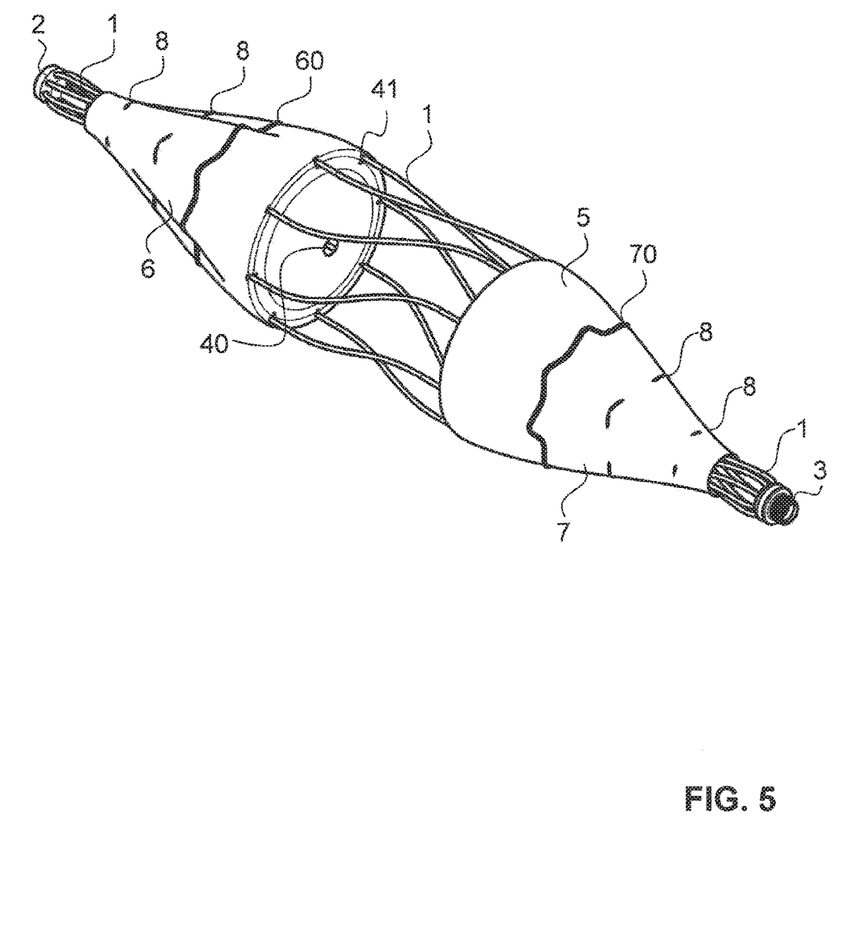
FIG. 5 shows the occluder according to FIG. 4 in a partly deployed or expanded state in a perspective view.
Figure 6:
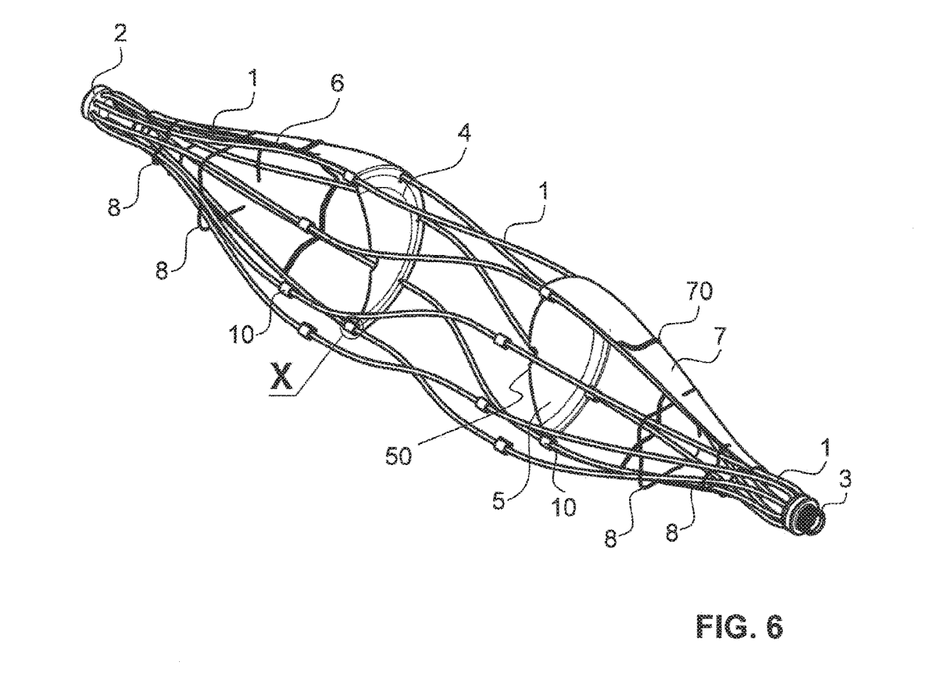
FIG. 6 shows the occluder according to FIG. 5 in a partial longitudinal section.
Figure 7:
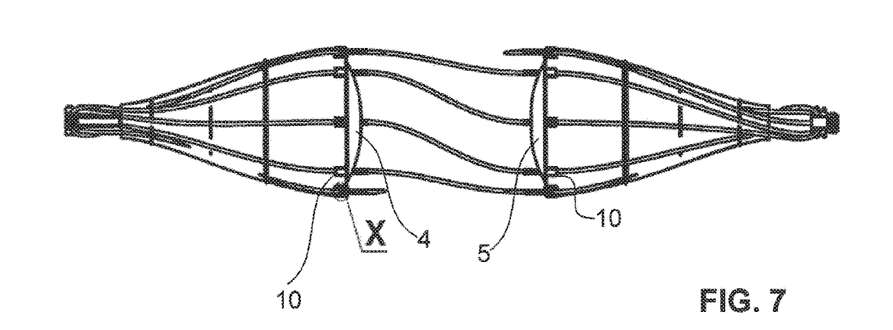
FIG. 7 shows the occluder of FIG. 4 in a longitudinal section view.
Figure 8:
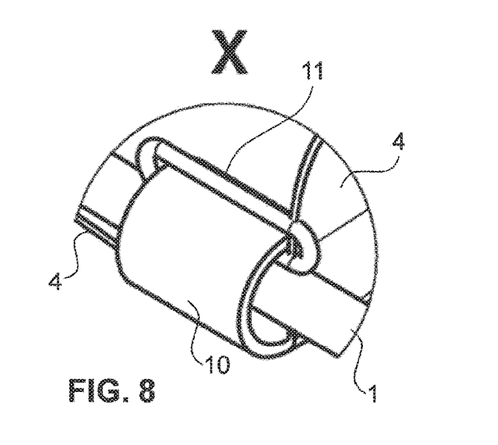
FIG. 8 shows an enlarged perspective view of a part of FIG. 6.

FIGS. 1 to 3 show a first embodiment according to the invention, the FIGS. 4 to 8 a second one. However the difference is only the way of sewing elongate members 1 to jackets 6, 7. The sewing thread bears the reference number 8 and the stitches are marked with the reference number 80.

Therefore these two embodiments will be described in the following together, the whole disclosure being applicable to both embodiments and no distinction is further made between the two embodiments.

The occluder comprises at least one, here two occluding bodies 4, 5, an expanding unit 1 and a locking unit 2, 3, as can be seen in FIGS. 1 to 3.

The expanding unit consists of a plurality of thin elongate members 1. These elongate members 1 are like filaments, wires or threads. They are flexible and can be bent, but preferably they have no elasticity in direction of their longitudinal axis. They are preferably stiff and inextensible. Each elongate member has a first end which is attached to or hold in a first holder 2 and a second end, which is attached to or hold in a second holder 3. The elongate members 1 are arranged separate from each other and are not directly connected to each other; i.e. they are preferably separate wires and not part of a net or otherwise connected.

When the two holders 2, 3 are brought together, the elongate members 1 are compressed longitudinally. They automatically bend and twist sideways to form two circular or loop shapes, similar to a flower, a propeller or an umbrella. These twisted shapes form fixation structures. These structures lay, when the occluder is implanted, on the surrounding tissue on both sides of the passage to be closed and fix the occluder at this position.

The two holders 2, 3 have locking elements which lock the occluder in this expanded shape and therefore lock the fixation structures in their shapes. One locking element is best seen in FIG. 3. It is a locking stem 20 of the first holder 2, which can be brought in engagement with an opening in the second holder 3.

Figure 10:
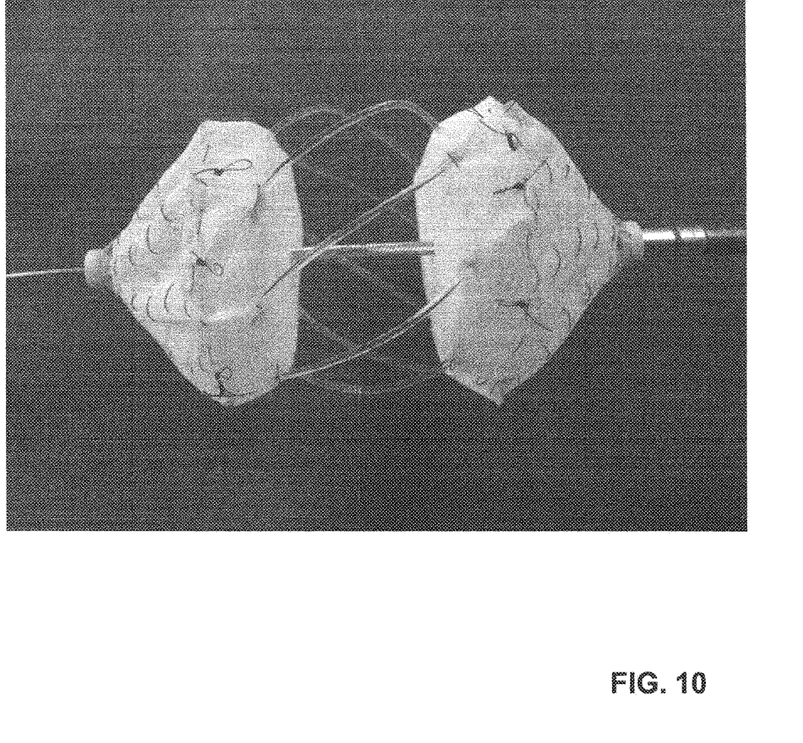
FIG. 10 shows a photo of the inventive occluder according the first embodiment.

The first and second occluding bodies 4, 5 are thin membranes, which are located between the two holders 2, 3. In their extended shape, they are preferably round, disk-shape and almost flat. They are made of a flexible material so that they can be folded or compressed when introduced into the introduction sheath. In the extended and deployed state of the occluder, they are extended as well. Preferably, they are almost flat, so that they can abut the surrounding tissue of the passage to be closed. In the figures, the occluding bodies appear to be quite stiff and their compressed and actual flexible shape is not realistically shown. Especially FIGS. 1 and 2 should not be understood in a way that the membranes 4, 5 and the jackets 6, 7 (which will be described later on) are stretched. Furthermore, in the situations shown in FIGS. 4 to 7 the two membranes 4, 5 are realistically more folded and less flat disk-like. The real occluder is shown in the photo according to FIG. 10. The seams 60 and 70, dividing the membranes 4, 5 from the jackets 6, 7 can well be seen. Preferably, the two occluding bodies 4, 5 are made of the same material each and have preferably the same size and shape each.

The occluding bodies 4, 5 extend in a radially manner from the longitudinal axis of the occluder. Preferably they are arranged concentrically to this axis. Also preferably, both membranes are identical and their distance to their neighboring holder 2, 3 is identical. Each occluding body 4, 5 comprise a central hole 40, 50. These holes 40, 50 as well as corresponding holes in the two holders 2, 3 are penetrated by the guide wire and the two delivery catheters when the occluder is introduced with an introduction sheath into the body passage.

The occluding bodies 4, 5 divide each of the elongate members 1 in three portions. A first portion lies between the first holder 2 and the first membrane 4. A second portion lies between the two membranes 4, 5 and the third portion lies between the second membrane 5 and the second holder 3. The first and third portions form in the expanded and twisted position the first and second fixation structure. The second portion has in this state a coil-like shape, as can best be seen in FIG. 2. Preferably at least the first and third portions of the elongate members 1 have the same length.

According to the invention, each rosette-like or flower-like fixation structure is individually surrounded by an own protecting jacket 6, 7 or shell. A first jacket 6, which is preferably a sleeve, is arranged around the first portion of the elongate members 1 and a second, preferably identical jacket 7 is arranged around the third portion of the elongate members 1. This can best be seen in FIGS. 1, 4 to 7.

The elongate members 1 can move relative to the jackets 6, 7. However to fix the position of the jackets 6, 7 so that they always lay over the first and third portions, the jackets 6, 7 are loosely attached to at least some of the elongate members 1 in this region. This is done in this example by threads 8, so that the jackets 6, 7 are sewed to the elongate members 1. This can best be seen in FIGS. 5 and 10.

The jackets 6, 7 themselves can be made of one single piece or they can be made of several parts which are connected to each other. In this example they are made of one single part each and are sewed to the membranes 4, 5 with sewing seams 60, 70.

The jackets 6, 7 are also attached to the membranes 4, 5, wherein the membranes 4, 5 form one face side of the jackets 6, 7. Preferably the jackets 6, 7 are sewed to the membranes 4, 5, so that they form a closed envelope or flexible shell which is open only for to small central holes on each side which are penetrated by the elongate members 1. Each occluding bodies 4, 5 however does always preferably form an approximately flat element when deployed and expanded, so that the occluding bodies 4, 5 can smoothly abut the surrounding tissue of the passage and close the passage in the most appropriate way.

As can best be seen in FIGS. 1 and 3 the fixation structures are enclosed within the shell formed by the jackets 6, 7 and the membranes 4, 5. Nevertheless, the fixation structure can still adapt its shape to the anatomical surrounding of the passage to be closed. As can be seen in FIGS. 1, 4 to 7 the parts of the expanding unit, i.e. the elongate members 1, which form the fixation structure in the expanded state, are also enclosed in these shells in the compressed or partly deployed state.

The inventive occluder has a new way to prevent relative movement between occluding bodies 4, 5 and the elongate members 1. The occluding bodies 4, 5 comprise on their circumference, in a substantial distance to their circumferential edge, holes 41. Each hole 41 is penetrated by one single elongate member 1. This can best be seen in FIG. 6. The holes are preferably arranged in evenly distances from each other.

The occluder also comprises fixations bushes 10. Each fixation bush 10 is penetrated by one single elongate member 1, wherein the bushes 10 are fixed to the elongate members 1, such that they are not moveable relative to the longitudinal axis of the respective elongate member. The bushes 10 are preferably crimped onto the elongate member 1.

Figure 9:
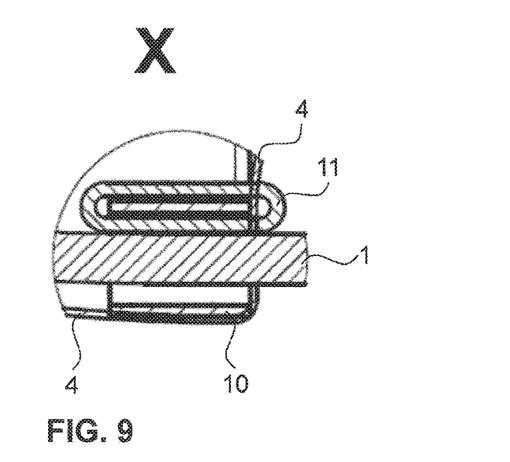
FIG. 9 shows a longitudinal section of the part of FIG. 8.

The bushes 10 are arranged on a first side of the membranes 4, 5, abutting this membrane 4, 5. This first side of the membrane is directed to the adjacent holder 2, 3 and the adjacent jacket 6, 7. The bushes 10 are sewed to the membranes 4, 5, as can be seen in FIG. 1. The sewing thread 11 penetrates the same hole of the bush 10 as the elongate member 1 and penetrates the membranes 4, 5 a second time adjacent to this hole. This can best be seen in FIGS. 8 and 9. The sewing thread 11 can form a closed loop as shown in the embodiment according to FIGS. 8 and 9. Each loop is formed by a separate thread.

Figure 11:
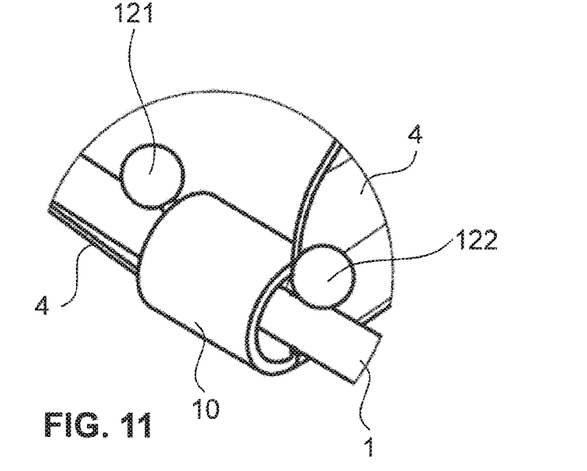
FIG. 11 shows an enlarged perspective view of a part of a third embodiment according to the invention and FIG. 12 shows a longitudinal section of the part of FIG. 11.
Figure 12:
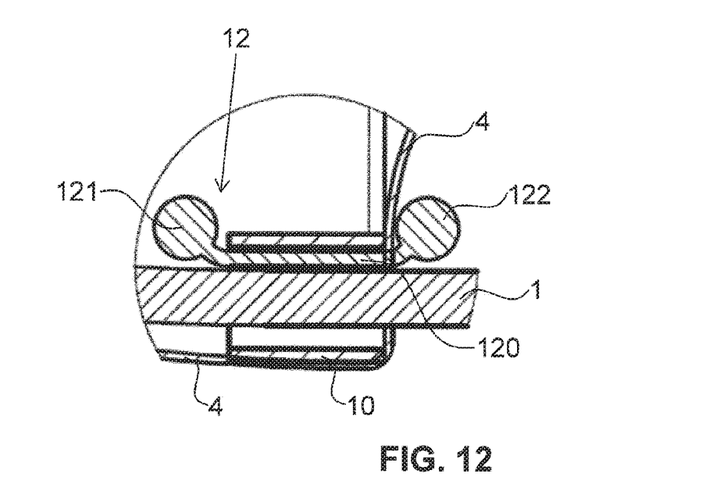

In the embodiment shown in FIGS. 11 and 12, the sewing thread 12 consist of a strand 120 and two free ends 121, 122 which are formed to bulges. Preferably these bulges are formed after the sewing thread 12 is pulled through the through hole of the bush 10. The ends can for example be heated or knotted in order to form the bulges. The thread does preferably not penetrate the membrane for a second time.

The bushes 10 of both membranes 4, 5 are located within the space or the chamber formed by the membrane 4 and jacket 6 and membrane 5 and jacket 7 respectively. This can best be seen in FIG. 7. Outside of the jacket, i.e. on the second side of the membranes 4, 5, no bushes 10 are present, only the sewing threads. When an elongate member breaks, the corresponding bush 10 remains attached to the membrane. When the thread is broken, the bushes 10 still remain within the jacket, especially when it is already filled with coagulated blood.

Even if no jacket is present, a membrane penetrated by elongate members but with fixation bushes sewed to the membrane is an improvement, since the tiny bushes can not wander within the human or animal body.

If the bushes are not sewed too tightly to the membranes, they still enable the membranes 4, 5 to move for only a short distance along the elongate members 1. Theses bushes 10 can also be used as X-ray markers, especially when the elongate members are invisible for X-ray.

The occluder according to the invention ensures that the tiny bushes can not wander within the human or animal body and improves even occluders already having protecting jackets.

The invention claimed is:

1. An occluder for occluding a passage in a circulatory system, the occluder comprising
   at least one occluding body for occluding the passage,
   a multiple of elongate members forming an expanding unit capable of expanding into at least one fixation structure for fixing the at least one occluding body within the passage thereby expanding the at least one occluding body, the elongate members passing through the at least one occluding body,
   a locking device capable of locking the expanding unit in an expanded state of the expanding unit; and
   fixation bushes for restricting relative movement between the elongate members and the at least one occluding body, each fixation bush surrounding one single elongate member, thereby forming an opening, and abutting one of the at least one occluding bodies,
   wherein the occluder further comprises at least one thread, and wherein at least one of said fixation bushes is fastened to the at least one occluding body with the at least one thread, the at least one thread penetrating said at least one fixation bush and the at least one occluding body, and
   wherein the at least one thread extends through the opening of said at least one fixation bush essentially parallel to the elongate member surrounded by said at least one fixation bush.

2. The occluder of claim 1, wherein the at least one occluding body comprises a multiple of openings, each opening being penetrated by one of the elongate members, and wherein the at least one thread penetrates the occluding body through these openings.

3. The occluder of claim 1, wherein the at least one thread forms a loop around each bush.

4. The occluder of claim 1, wherein each fixation bush is fastened to the at least one occluding body with a separate thread.

5. The occluder of claim 4, wherein each thread is forming a closed loop.

6. The occluder of claim 4, wherein each thread comprises a strand with a first free end and a second free end, the first free end being located on one side of each fixation bush and the second free end being located on a second, opposite side of each fixation bush, and wherein the first and second free end are thicker than the strand in between.

7. The occluder of claim 6, wherein the first free end and the second free end are bulges.

8. The occluder of claim 1, wherein the occluder comprises a jacket which envelops the elongate members at least partially.

9. The occluder according to claim 8, wherein the jacket envelops at least one of the at least one fixation structures.

10. The occluder of claim 8, wherein the jacket is attached to the at least one occluding body.

11. The occluder according to claim 10, wherein the at least one fixation bush is arranged in a space defined by the jacket and the at least one occluding body.

12. The occluder according to claim 11, wherein all fixation bushes are arranged in the space defined by the jacket and the at least one occluding body.

13. The occluder according to claim 1, wherein the occluder comprises exactly two fixation structures.

14. The occluder according to claim 1, wherein the occluder comprises exactly two outer jackets and at least two fixation structures and wherein each outer jacket envelopes one of the fixation structures, wherein the two outer jackets envelop different fixation structures.

15. The occluder according to claim 1, wherein the occluder comprises exactly a first and a second occluding body, wherein in a non-expanded state the first and second occluding bodies are arranged at a distance from each other, wherein a first of said fixation structures is arranged between the first occluding body and a first element of the locking device and a second of said fixation structures is arranged between the second occluding body and a second element of the locking device.

16. The occluder according to claim 1, wherein the at least one occluding body is a flexible sheet.

* * * * *